(12) United States Patent
Fujita et al.

(10) Patent No.: US 9,260,805 B2
(45) Date of Patent: Feb. 16, 2016

(54) BASE FABRIC FOR STENT GRAFT, AND STENT GRAFT

(75) Inventors: Kazuya Fujita, Otsu (JP); Tomoyuki Horiguchi, Otsu (JP); Ryo Matsuo, Osaka (JP); Kazuhiro Tanahashi, Otsu (JP); Asanori Shimada, Otsu (JP)

(73) Assignee: TORAY INDUSTRIES, INC., Tokyo (JP)

( * ) Notice: Subject to any disclaimer, the term of this patent is extended or adjusted under 35 U.S.C. 154(b) by 144 days.

(21) Appl. No.: 13/643,202

(22) PCT Filed: Apr. 27, 2011

(86) PCT No.: PCT/JP2011/060203
§ 371 (c)(1),
(2), (4) Date: Oct. 24, 2012

(87) PCT Pub. No.: WO2011/136243
PCT Pub. Date: Nov. 3, 2011

(65) Prior Publication Data
US 2013/0041452 A1    Feb. 14, 2013

(30) Foreign Application Priority Data

Apr. 28, 2010 (JP) ................... 2010-103197
Apr. 28, 2010 (JP) ................... 2010-103198
Apr. 28, 2010 (JP) ................... 2010-103200

(51) Int. Cl.
*D03D 15/00* (2006.01)
*D04B 21/16* (2006.01)
(Continued)

(52) U.S. Cl.
CPC *D04B 21/16* (2013.01); *D03D 1/00* (2013.01); *D03D 13/008* (2013.01); *D03D 15/0061* (2013.01); *A61F 2/07* (2013.01);
(Continued)

(58) Field of Classification Search
CPC .............................. A61F 2/2418; D03D 15/00
USPC ........................................................ 623/1.13
See application file for complete search history.

(56) References Cited

U.S. PATENT DOCUMENTS

2003/0028239 A1* 2/2003 Dong ........................ 623/1.13
2003/0176911 A1   9/2003 Iancea et al.
2005/0085894 A1   4/2005 Kirshner
2006/0009835 A1   1/2006 Osborne et al.

FOREIGN PATENT DOCUMENTS

DE  10 2007 032 156 A1  10/2008
EP         1 086 663 A1   3/2001
(Continued)

OTHER PUBLICATIONS

International Search Report dated Aug. 2, 2011, application No. PCT/JP2011/060203.
Extended European Search Report for EP 11775024.0-1710 Which Corresponds to PCT/JP2011/060203; Issued Feb. 24, 2014.

*Primary Examiner* — Thomas J Sweet
*Assistant Examiner* — Matthew Schall
(74) *Attorney, Agent, or Firm* — Ratnerprestia

(57) ABSTRACT

A base fabric for a stent graft is a woven fabric constituted by a fiber having a total fineness of 1 to 40 decitex and a single yarn fineness of 0.1 to 2.0 decitex and has a yarn density of 150 strands/2.54 cm or more in both longitudinal direction and lateral direction, a thickness of 1 to 90 μm, and a tensile strength of 50.0 N/cm or more in both longitudinal direction and lateral direction. According to the present invention, the base fabric for a stent graft having thinness, high strength, low permeability, durability, and flexibility can be obtained.

6 Claims, 3 Drawing Sheets

(51) Int. Cl.
  *D03D 1/00* (2006.01)
  *D03D 13/00* (2006.01)
  *A61F 2/07* (2013.01)

(52) U.S. Cl.
  CPC .... *D10B 2321/021* (2013.01); *D10B 2321/042* (2013.01); *D10B 2331/02* (2013.01); *D10B 2331/04* (2013.01); *D10B 2331/10* (2013.01); *D10B 2509/06* (2013.01); *Y10T 442/3065* (2015.04); *Y10T 442/3089* (2015.04)

(56) References Cited

FOREIGN PATENT DOCUMENTS

| | | |
|---|---|---|
| JP | 11-104153 A | 4/1999 |
| JP | 2000-225198 A | 8/2000 |
| JP | 2005-118570 A | 5/2005 |
| JP | 2008-505713 | 2/2008 |

\* cited by examiner

BASE FABRIC FOR STENT GRAFT, AND STENT GRAFT

CROSS REFERENCE TO RELATED APPLICATIONS

This is the U.S. National Phase application of PCT International Application No. PCT/JP2011/060203, filed Apr. 27, 2011, and claims priority to Japanese Patent Application Nos. 2010-103200, filed Apr. 28, 2010, 2010-103198, filed Apr. 28, 2010, and 2010-103197, filed Apr. 28, 2010, the disclosures of each of which are incorporated herein by reference in their entireties for all purposes.

FIELD OF THE INVENTION

The present invention relates to instruments for reconstruction or repair of aneurysms. Particularly, the present invention relates to a stent graft for reconstruction or repair of an aneurysm such as an abdominal aortic aneurysm or a thoracic aortic aneurysm, which stent graft is transported percutaneously or transluminally. The present invention also relates to a base fabric for a stent graft, which is used in a stent graft.

BACKGROUND OF THE INVENTION

Aneurysms, which are abnormal dilatations of arterial walls, are abdominal aortic and thoracic aortic aneurysms. The abdominal aortic aneurysm is usually an aneurysm in the abdominal part of an artery located in the vicinity of two iliac arteries or near renal arteries. In addition, the thoracic aortic aneurysm is an aneurysm in the thoracic part of the aorta. There is the risk of rupturing an aneurysm to cause fatal massive bleeding if the aneurysm is left unattended without being treated.

A surgical bypass operation is usually performed for treatment of an abdominal aortic aneurysm. In this operation, a graft is placed in an affected part or a dilated segment. This operation, which is a treatment technique by incision by a transperitoneal or retroperitoneal procedure, the treatment technique of resecting an aneurysmal part and replacing a resected part with a synthetic graft, has been risky. Complications due to the operation include myocardial ischemia, renal failure, impotence, intestinal ischemia, infections, lower limb ischemia, spinal cord injuries with paralysis, aorta-internal organ fistulas, and the like. In the worst case, death is caused. Surgical treatment of an abdominal aortic aneurysm has a high mortality rate.

Also, the surgical treatment of an abdominal aortic aneurysm has such problems that its mortality rate is high, a recovery period is prolonged because of making a great incision of the abdomen and opening the abdominal cavity, it is difficult to suture a graft to the aorta, natural thrombotic activity which supports and strengthens the graft is lost, and emergency surgery is required when an artery is ruptured. In addition, since many patients with abdominal aortic aneurysms are elderly and therefore may have other chronic diseases such as cardiac disease, lung disease, liver disease, and (or) renal disease, it cannot be said that they are ideal for persons targeted for the operation.

When an aneurysm is generated in the thoracic aorta, reconstruction by an operation is a treatment method performed widely, like the case of the abdominal aortic aneurysm. In this operation, treatment of replacing an aneurysm segment with a prosthesis instrument is performed. However, this operation always has a high risk as described above as well as has a high mortality rate and a high morbidity rate.

On the other hand, a lot of researches on treatment methods using catheters have been conducted. The treatment methods using catheters have been facilitated by development of stent grafts. The treatment methods can shorten a period in which a patient is in a hospital and an ICU and have an advantage that a morbidity rate and a mortality rate due to an operation are low.

Generally, a surgical incision of an artery distant from an affected part, such as a common femoral or brachial artery, is made to transport a stent graft through a catheter inserted therefrom to the affected part under fluoroscopy. An introducer with an appropriate size is fitted in a guide wire, and the catheter and the guide wire are passed into an aneurysm. Then, the stent graft is advanced to an appropriate position along the guide wire through the introducer. Most stent grafts are self-expandable but may require an additional intracatheter procedure, such as balloon angioplasty, for fixing the position of a stent graft. A standard angiogram can be obtained by injecting an X-ray contrast medium into an affected part following the placement of the stent graft.

Since the above-mentioned catheter has a large diameter of typically around 20 French (Fr) (3 Fr=1 mm), it cannot be said that it is lowly invasive in the current situation, and reconstruction by a surgical operation is necessary for closure of the incised part of an artery. In addition, patients with small vessels are out of the scope of its application, since it is difficult to insert a stent graft, and have not yet retained the benefit of this treatment. Accordingly, it is necessary to design a stent graft that can be held by a catheter with a smaller diameter. Specifically, such thought as to narrow a stent and a fabric when being folded and to keep flexibility is put into the stent graft to enable its insertion into even minimum vessel when it is inserted into a vessel and/or the like.

It is conceivable that a conventional fabric is more thinned for improvement in a base fabric for a stent graft. However, when it is simply thinned, there are the problems of decreasing the strength of the fabric and increasing its permeability. Thus, disclosed is a base fabric on the surface of which microfibers are raised and which has a thickness of 0.2 mm or less in the state where the base fabric is compressed during insertion and has a thickness of 0.4 mm or more after placement into a vessel (e.g., see Patent Literature 1). Also, disclosed is the technology of making yarn constituting a woven fabric and/or the like have 5 to 40 denier to make a thin structure (see Patent Literature 2).

PATENT LITERATURE

Patent Literature 1

Japanese Patent Laid-Open No. 2000-225198

Patent Literature 2

National Publication of International Patent Application No. 2008-505713

SUMMARY OF THE INVENTION

A base fabric having a raised surface as in Patent Literature 1 has the feature of varied thicknesses when compression and opening are performed. However, a raised fabric structurally has an absolute thickness and, for example, it is difficult to make a base fabric have a thickness of 90 μm or less. Further, since raised fibers are entangled with each other to tense a texture when it is compressed even if it is flexible in a raising state, for example, it is difficult to insert it into a catheter of 18 Fr or less.

In addition, since the raised fabric has a rough structure when it is raised, it has the effect of accelerating positive adsorption of a cell on raised fibers, while fiber density is low and it tends to be poor in strength. In addition, since permeability is increased to lead to leakage of blood and a contrast medium, it is not preferred.

Use of yarn with low fineness as in Patent Literature 2 is effective for producing a thin substrate, but it is not easy to impart the substrate with strength without processing such as coating.

Specifically, since the strength of a woven fabric tends to decrease when yarn is thinned, keeping of specific strength is limited. In addition, shortening of a distance between strands of yarn for decreasing permeability necessarily leads to increase in yarn density. Therefore, it is difficult to reduce the absolute thickness of a woven fabric substrate, and thinning of a substrate for a stent graft to enable insertion into a thinner catheter is limited. Although, for compensation therefor, a coating may be applied to the woven fabric to thin the base fabric by imparting the woven fabric substrate with even thin yarn with sufficient strength, the durability of a film agent is problematic due to the coating. Accordingly, any means that satisfies all of thinness, high strength, low permeability, durability, and flexibility has not been found.

The base fabric for a stent graft according to an exemplary embodiment of the present invention is a woven fabric comprising a fiber having a total fineness of 1 to 40 decitex and a single yarn fineness of 0.1 to 2.0 decitex and has a yarn density of 150 strands/2.54 cm or more in both longitudinal direction and lateral direction, a thickness of 1 to 90 µm, and a tensile strength of 50.0 N/cm or more in both longitudinal direction and lateral direction. In addition, the stent graft according to an aspect of the present invention comprises the base fabric for a stent graft according to the present invention and a stent.

According to the present invention, a base fabric for a stent graft having thinness, high strength, low permeability, durability, and flexibility can be obtained. In addition, a stent graft which can be inserted into a thinner catheter can be provided.

DETAILED DESCRIPTION OF EMBODIMENTS OF THE INVENTION

Figure 1:
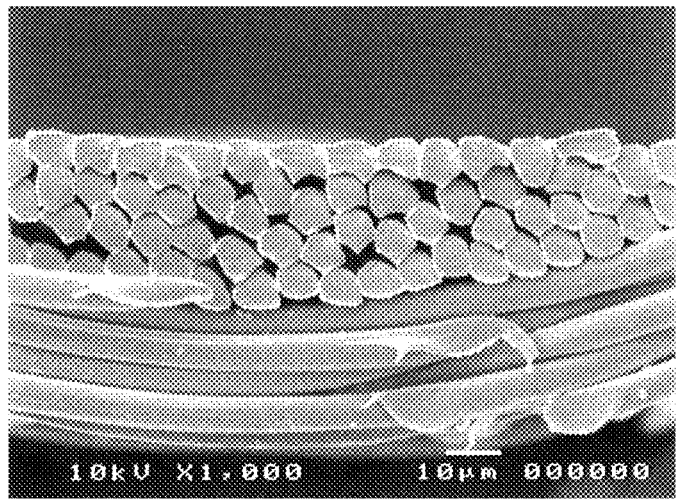
FIG. 1 is a macrophotograph at 1000 times of an example of a cross-sectional shape having generally parallel sides on the outermost surface of a cloth.

The base fabric for a stent graft according to an embodiment of the present invention is a woven fabric. The structure of the fabric is a woven fabric, a knitted fabric, a nonwoven fabric, or the like, but a woven fabric is advantageous for compatibility between thinness and strength.

In accordance with the present invention, "longitudinal direction" is the warp direction of the woven fabric. "Lateral direction" is the weft direction of the woven fabric.

The thickness of the woven fabric is 1 to 90 µm. The lower limit of the thickness is preferably 10 µm or more. The upper limit of the thickness is preferably 80 µm or less, more preferably 90 µm or less. In the case of 90 µm or less, it can be inserted even into a thin catheter of 18 Fr or less. In the case of 1 µm or more, strength can be maintained.

A fiber constituting the woven fabric is not particularly limited if it is a polymer having biocompatibility. For example, polyesters, polyethylenes, polytetrafluoroethylenes, polyurethanes, polyamides, nylons, and/or the like may be used. Among them, the polyesters, particularly polyethylene terephthalate, are preferred in terms of excellent strength.

The total fineness of the fiber is 1 to 40 decitex. The lower limit of the total fineness is preferably 5 decitex or more, more preferably 10 decitex or more. The upper limit of the total fineness is preferably 35 decitex or less, more preferably 25 decitex or less. In the case of 1 decitex or more, strength necessary for the base fabric can be maintained. In the case of 40 decitex or less, the thickness of the base fabric can be reduced.

The single yarn fineness of the fiber is 0.1 to 2.0 decitex. The lower limit of the single yarn fineness is preferably 0.3 decitex or more. The upper limit of the single yarn fineness is preferably 1.0 decitex or less, more preferably 0.5 decitex or less. In the case of 0.1 decitex or more, the yarn strength of the single yarn is not deteriorated and rupture due to wear can be suppressed. In the case of 2.0 decitex or less, flexibility can be given to the base fabric.

The fiber is preferably multifilament rather than monofilament in terms of wear resistance and flexibility. Flexible management of force from the outside can be performed to express softness due to the slip and displacement of constituting single yarn by making it multifilament. Multifilament form may be zero twist, false twist yarn, or twisted yarn, but, since fibers easily converge in the case of the twisted yarn, the zero twist or false twist yarn is preferred for having compatibility between thinness and low permeability while being excellent in the above-described effect.

As the structure of the woven fabric, which is a plain weave, a twill weave, a satin weave, a double woven fabric, a hollow weave, or the like without particular limitation, the plain weave or the twill weave is preferred in terms of easy compatibility between the thinness and strength of the base fabric.

By adopting the constitution of the present invention, a woven fabric can also be imparted with flexibility since yarn fineness is low. Weaving density may be decreased to achieve the base fabric excellent in flexibility, particularly having a cantilever bending resistance of 50 mm or less in terms of stiffness in longitudinal and lateral directions as mentioned below, but permeability is then increased. A high-density woven fabric generally has a tensed texture but can be imparted with flexibility even if yarn density is increased when a fiber having a total fineness of 1 to 40 decitex and a single yarn fineness of 0.1 to 2.0 decitex is used.

When permeability is suppressed, particularly when permeability is made to be 250 mL/(cm$^2$·min) or less, it is necessary to closely weave a woven fabric, but the woven fabric with a tensed texture is then made. Although there is a trade-off relationship between flexibility and permeability as described above, flexibility can be maintained even if yarn density is increased in the case of the base fabric for a stent graft according to the present invention as mentioned above. That is, compatibility between flexibility and low permeability can be achieved.

In addition, necessary strength is secured if a woven fabric has a tensile strength of 50.0 N/cm or more in longitudinal and lateral directions. It is preferably 55.0 N/cm or more, more preferably 60.0 N/cm or more. Although increase in longitudinal density and decrease in lateral density are generally preferred form in terms of a weaving property when a high-density woven fabric is woven, then, tensile strength in a longitudinal direction is increased but tensile strength in a lateral direction is decreased, so that sufficient woven fabric strength is not obtained. Since a stent graft is repeatedly stretched and shrunk in all directions in a vessel, it is cut in the direction of yarn having low tensile strength of a woven fabric to be a substrate to rupture the woven fabric. For preventing this, tensile strengths of 50.0 N/cm or more in both longitudinal direction and lateral direction of the woven fabric are necessary. In the case of the tensile strengths of 50.0 N/cm or more in the longitudinal and lateral directions of the woven fabric, it is not necessary to perform a procedure, such as coating or bonding, for applying strength to the woven fabric. Therefore, the problem of decrease in the strength of the woven fabric due to deterioration of a coating film can be prevented. The upper limit of the tensile strength is not particularly limited; however, since, when it exceeds 100 N/cm, the strength-elongation balance of yarn is lost to increase the bending stiffness of the woven fabric, the tensile strength is preferably 100 N/cm or less.

For making the woven fabric have a tensile strength of 50.0 N/cm or more in the longitudinal direction and the lateral direction, it is necessary to have a yarn density of 150 strands/2.54 cm or more in both longitudinal direction and lateral direction. For example, when the yarn density in the lateral direction is less than 150 strands/2.54 cm even if the yarn density in the longitudinal direction is 150 strands/2.54 cm or more, there is the risk of rupture in the living body when it is used as a substrate for a stent graft since tensile strength in a weft direction is decreased. Specifically, for applying characteristics necessary as a base fabric for a stent graft, it is important to keep the balance of the yarn densities in the longitudinal direction and the lateral direction. In addition, the yarn densities in the longitudinal direction and the lateral direction are preferably similar. For example, when the yarn density in the longitudinal direction is 450 strands/2.54 cm and the yarn density in the lateral direction is 150 strands/2.54 cm, the degree of freedom of the warp is decreased since the yarn density in the longitudinal direction is high, so that stress per warp strand due to external force may be increased while the strength of the woven fabric may be decreased. Accordingly, the balance of the yarn densities in the longitudinal direction and the lateral direction is preferably within a specific range. Specifically, a yarn density balance represented in the following expression is preferably 2.0 or less, more preferably 1.8 or less, further preferably 1.5 or less.

Yarn density balance=(yarn density in direction with high density)/(yarn density in direction with low density).

The tensile strength of a woven fabric as used herein is obtained by a method described in the JIS L 1096 8.12.1 A method (stripping method) (1999), in which the arithmetic means of three rupture strengths (N/cm) per centimeter in width in a longitudinal direction and a lateral direction are calculated, respectively, to be given to three significant figures.

The surface of the woven fabric is preferably unraised. Since a thickness is increased by raising and a fiber is cut by the raising, strength may also be decreased. Due to the smooth surface of the woven fabric, the base fabric becomes slippery and is folded to be small to be easily held by a catheter.

In the base fabric for a stent graft according to the present invention, the woven fabric preferably has a cover factor (hereinafter abbreviated as CF) of 1300 to 4000 from the viewpoint of compatibility between strength and thinness. The lower limit of CF is more preferably 1400 or more, further preferably 1500 or more. The upper limit of CF is more preferably 3500 or less, further preferably 3000 or less. As used herein, CF is calculated by the following expression:

$$CF = \sqrt{A} \times N + \sqrt{B} \times M$$

A: Fineness (decitex) of warp, B: Fineness (decitex) of weft

N: The number (strands/2.54 cm) of warp, M: The number (strands/2.54 cm) of weft.

In the case of a woven fabric having a ripstop as described below, CF is calculated using fineness obtained by averaging the fineness of fibers constituting the ripstop and the fineness of fibers that do not constitute the ripstop. In doing so, it can easily be calculated if a unit texture is used. For example, the mean fineness of a woven fabric including a ripstop with two strands of yarn of 56 decitex and a ground part, which is not a ripstop, with four strands of yarn of 22 decitex as unit textures is $((56 \times 2)+(22 \times 4))/6=33.3$ decitex.

When CF is 1300 or more, high strength can be maintained even in the case of low fineness while decreasing a thickness. Higher CF is preferred in terms of improvement in strength; however, since a weaving property may be deteriorated with increasing CF to cause damage to yarn, particularly deterioration of quality, such as fluff or decrease in yarn strength, it is preferably 4000 or less.

When the woven fabric has a yarn density of 150 strands/2.54 cm or more in both longitudinal direction and lateral direction, a sufficient permeability suppression effect can be shown. It is preferably 160 strands/2.54 cm or more, further preferably 180 strands/2.54 cm or more, in both longitudinal direction and lateral direction. In addition, it is preferably 430 strands/2.54 cm or less, further preferably 400 strands/2.54 cm or less, in both longitudinal direction and lateral direction.

The base fabric for a stent graft according to an embodiment of the present invention has the feature of particularly having excellent flexibility and preferably has a cantilever bending resistance of 10 to 50 mm. The cantilever bending resistance is preferably 40 mm or less, more preferably 30 mm or less. The cantilever bending resistance of 50 mm or less facilitates insertion into a thinner catheter. On the other hand, although the effect of the present invention can be shown even if the cantilever bending resistance is less than 10 mm, it is preferably 10 mm or more from the viewpoint of strength.

While decrease in fineness or decrease in yarn density offers flexibility as mentioned above, permeability is increased and strength is decreased. In accordance with an aspect of the present invention, a fiber with specific yarn density enables compatibility between them at a high level. Multifilamentation is also an effectual measure for improving flexibility. Further, the effect of also having thinness can be obtained in accordance with the present invention.

A value determined by the JIS L1096 8.19. 1 A method (cantilever method) (1999) is used as cantilever bending resistance. In accordance with the present invention, it refers to a mean value in a longitudinal direction and a lateral direction.

The base fabric for a stent graft according to the present invention preferably has a permeability of 250 mL/(cm²·min) or less. It is more preferably 200 mL/(cm²·min) or less, further preferably 100 mL/(cm²·min) or less. If it is 250 mL/(cm²·min) or less, leakage of blood and a contrast medium can permanently be suppressed.

The permeability according to the present invention is the mean value of two measured values of the amounts of water permeating through each sample obtained by sampling two spots from a specimen at random. A specific measurement method will be described below.

The base fabric for a stent graft according to the present invention preferably includes an outermost layer of at least one surface of the woven fabric, which outermost layer contains (i) a fiber with a cross-sectional shape having a side which is generally parallel to a central line of a thickness of the woven fabric and/or (ii) a fiber with a cross-sectional shape having a major axis which is generally parallel to a central line of the thickness of the woven fabric. As used herein, "central line of a thickness of a woven fabric" refers to a line which connects center points in the thickness direction of the woven fabric. The side or major axis at an angle 20° or less with respect to the central line of the thickness of the base fabric is "generally parallel". Such a side or a major axis is more preferably at 10° or less, particularly preferably at 5° or less, with respect to the central line of the thickness of a substrate. Even in the case of a woven fabric comprising fibers having a cross-sectional shape such as an ordinary circle or a triangular hollow, the outermost surface preferably contains fibers transformed into a cross-sectional shape having a side which is generally parallel to the central line of the thickness of the woven fabric. Alternatively, in the case of a woven fabric comprising fibers having a flat cross-sectional shape, the outermost surface preferably contains fibers of which the major axis direction is generally parallel to the central line of the thickness of the woven fabric. Such a woven fabric enables compatibility between low permeability and flexibility at a further high level since permeability can be decreased even if fineness is low or yarn density is low. In addition, the above-described fibers (i) and/or (ii) are more preferably contained in the outermost layers of both front and back surfaces of the woven fabric. In addition, all the fibers of the outermost layers of the woven fabric are more preferably the above-described fibers (i) and/or (ii).

For obtaining the above-described fiber (i), mentions is made of measures of weaving with a fiber having a cross section such as a circle or a triangle and thereafter performing press treatment with a calender machine or the like, measures of wearing and grinding it, and the like. The measures of performing press treatment with the calender machine or the like are preferred to achieve compatibility between low permeability and flexibility at a higher level.

In the base fabric for a stent graft according to the present invention, it is preferable to further incorporate a ripstop to make a plain woven fabric in order to keep strength and durability for being able to endure the external force of blood pressure and pulsation acting from every direction over an age unit. In this plain woven fabric into which the ripstop is incorporated, the ground part other than the ripstop part comprises the fiber having a total fineness of 1 to 40 decitex and a single yarn fineness of 0.1 to 2.0 decitex as explained above.

Although the size of a lattice design constituted by the ripstop is not particularly limited, the size of the lattice design is 2 mm or less in both longitudinal direction and lateral direction to give strength while keeping the flexibility and thinness of a cloth. Even in the event of occurrence of damage such as fraying during use in the body, the growth of a flaw can be stopped at a ripstop portion. For this, the size of the lattice design is preferably 2 mm or less.

Although, in the fibers constituting the ripstop, the same two or more fibers as the fibers which do not constitute the ripstop may neatly be placed and different kinds of yarn may also be placed, the fineness of the fibers constituting the ripstop is preferably more than the fineness of the fibers which does not constitute the ripstop. Specifically, the fineness of the fibers constituting the ripstop is preferably 44 decitex or more. As a result, not only tear strength but also tensile strength can be increased, and a cloth which is durable and hard to loose its shape can also be made.

The surface of the base fabric for a stent graft according to the present invention is preferably subjected to hydrophilic working. The hydrophilic working according to the present invention may be coating or grafting of a hydrophilization agent on a fiber surface. Examples of the hydrophilization agent may include, e.g., polyvinyl alcohol, polyethylene oxide, polyvinylpyrrolidone, and the like. The hydrophilic working enables formation of the surface which is more adsorbed by a cell and is superior in biocompatibility. Also, the effect of swelling in a seam and/or the like to deteriorate permeability due to a filling effect can be expected depending on the hydrophilization agent.

The stent graft according to the present invention comprises the base fabric for a stent graft according to the present invention and a stent. In the stent graft, at least one stent is fixed on the base fabric for a stent graft with a suture and/or the like. A stent design is not particularly limited, but mention may be made of, for example, self-expandable stents and balloon-expandable stents. Stent materials include shape memory alloys, such as for example nickel titanium alloys, and the like.

An example of a method for producing the base fabric for a stent graft and the stent graft according to the present invention will now be mentioned without limitation to the production method described herein.

Fibers constituting the woven fabric according to the present invention may be obtained by direct spinning or may be obtained by performing composite spinning using a sea-island type or fiber-splitting type composite spinneret to make a woven fabric, followed by making it ultrafine. The former is preferred in terms of a cost.

The fibers obtained in such a manner are then made into a woven fabric. A weaving machine which produces the woven fabric is not particularly limited but shuttleless weaving machines such as water jet weaving machines and air jet weaving machines, Fly shuttle weaving machines, tappet weaving machines, Dobby weaving machines, Jacquard looms, and the like may be used. After weaving, as needed, scouring and relaxation treatment are performed to perform heat set by a tenter and/or the like.

Then, the woven fabric may also be subjected to press treatment by a calender machine or the like. During this, the surface of the calender machine or the like is preferably heated at a temperature that is not less than the glass transition point or softening point of a polymer constituting the fibers. By this treatment, the cross-sectional shape of a fiber on a surface portion contacting with the calender machine or the like is transformed into a shape having a side which is generally parallel to the surface. For example, in the case of a polyester fiber, heating is preferably performed to increase the temperature of the calender machine or the like to around 120 to 180° C. to perform the treatment.

When the above-described press treatment is performed, hydrophilization treatment may be performed either before or after it, or both thereof. As a method for hydrophilization treatment includes, mention is made of, e.g., a method of subjecting a hydrophilization agent to coating treatment or plasma and corona treatment to activate the surface of a fiber and thereafter treating the hydrophilization agent to perform graft treatment.

The base fabric for a stent graft obtained in such a manner is cut into a necessary size by fusion cutting or the like and thereafter equipped with a stent to make a stent graft. This equipment method, which is not particularly limited, may be performed by, for example, a method of sewing using a suture such as polyester.

The stent and the graft may also be integrated in such a manner, followed by coating a hydrophilization agent to close a seam.

EXAMPLES

The present invention will be explained in detail below with reference to examples. As a method for measuring each physical property value in examples, a method below is used.

A. Thickness

The thickness of a woven fabric was measured using a thickness gauge to the measurement of Paper and similar objects (manufactured by Ozaki Mfg. Co. Ltd., trade name "Peacock H"). The woven fabric was sandwiched at a pressure of 23.5 kPa to determine a measured value (μm) after left unattended for 10 seconds. Five spots in total were similarly measured at random. The arithmetic mean value of the five measurement values was determined to obtain as the thickness of the woven fabric a value (μm) by rounding off the arithmetic mean value to the nearest integer.

B. Permeability

Two spots were sampled from the woven fabric at random, measurement of each sample was performed twice by a method described below to determine four values in total, and the arithmetic mean value of the four values was used as permeability.

A woven fabric specimen measuring 2 cm per side was sandwiched between two pieces of doughnut-like packing of 4 cm in diameter, from which parts of 1 cm in diameter were punched, not to have any part, through which liquid passes, other than the punched parts. This was held in a housing for a circular filtration filter. A reverse osmotic membrane filtrate at a temperature of 25° C. was passed through this circular filtration filter for 2 minutes or more until the woven fabric specimen sufficiently retained the liquid. External pressure dead-end filtration of the reverse osmotic membrane filtrate was performed for 30 seconds under the conditions of a temperature of 25° C. and a filtration differential pressure of 120 mmHg, and the permeation amount (mL) of water permeating through the parts of 1 cm in diameter was measured. The permeation amount was determined by being rounded off to the nearest integer. The permeation amount (mL) was converted into a value per unit time (min) and effective woven fabric area ($cm^2$) to determine a water permeance ability at a pressure of 120 mmHg.

C. Cantilever Bending Resistance

It was measured based on the JIS L 1096 8.19. 1A method (cantilever method) (1999). A value obtained by averaging two values obtained in both longitudinal direction and lateral direction was used as the cantilever bending resistance.

D. Tensile Strength

It was measured based on the JIS L 1096 8.12. 1A method (stripping method) (1999). A sample of 5 cm in width and 20 cm in length with the longitudinal direction of the woven fabric as a lengthwise direction was collected and was extended at a tension speed of 10 cm/min by a tensile tester of constant rate extension type at a length of 10 cm between grips. The obtained value was converted into tensile strength (N/cm) per centimeter in width. This was performed for three samples, and the arithmetic mean value of the three obtained values was used as tensile strength (N/cm) in the longitudinal direction. Similar measurement of a sample of 5 cm in width and 20 cm in length with the lateral direction of the woven fabric as a lengthwise direction was also performed as tensile strength (N/cm) in the lateral direction.

E. Cross-Section Observation

The cross section of the woven fabric was observed with a scanning electron microscope (SEM). Two spots either in the cross section perpendicular to the longitudinal direction of the woven fabric or in the cross section perpendicular to the lateral direction were sampled to observe strands of yarn in the vicinities of their surfaces at 1000 times and 3500 times.

Example 1

A polyethylene terephthalate fiber of 22 decitex and 12 filaments was used to be weaved into a plain weave in a water jet loom. This was scoured, dried, and set to make a woven fabric with a finished yarn density of 250 strands/2.54 cm in a longitudinal direction and 200 strands/2.54 cm in a lateral direction and a cover factor of 2111. The obtained woven fabric was thin and had low permeability and excellent flexibility.

Example 2

A woven fabric was made in the same manner as in Example 1 except a finished yarn density of 220 strands/2.54 cm in a longitudinal direction and 210 strands/2.54 cm in a lateral direction. Then, only one roll was overheated to 160° C. to be subjected to calender treatment and was thermally set at 180° C. The obtained woven fabric was thin and had low permeability.

Example 3

A woven fabric was made in the same manner as in Example 1 except that the fiber was a polyethylene terephthalate fiber of 22 decitex and 48 filaments and had a finished yarn density of 300 strands/2.54 cm in a longitudinal direction and 200 strands/2.54 cm in a lateral direction. The obtained woven fabric had further suppressed permeability and excellent flexibility in comparison with the woven fabric of Example 1.

Example 4

A woven fabric was made in the same manner as in Example 1 except a finish yarn density of 160 strands/2.54 cm in a longitudinal direction and 160 strands/2.54 cm in a lateral direction. The obtained woven fabric had increased permeability but was thin and also excellent in flexibility in comparison with the woven fabric of Example 1.

Example 5

For the woven fabric obtained in Example 4, only one roll was further overheated to 160° C. to be subjected to calender treatment and was thermally set at 180° C. The obtained woven fabric was thin and had low permeability and excellent flexibility.

Figure 2:
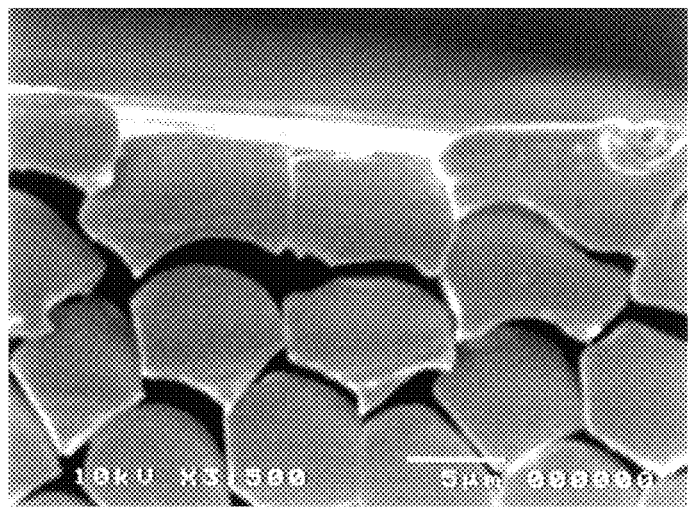
FIG. 2 is a macrophotograph at 3500 times, in which a part of FIG. 1 is further enlarged.

When the cross section of the obtained woven fabric was observed with an SEM, strands of yarn in a surface layer were transformed to be generally parallel to a surface (generally perpendicular to a thickness direction). FIG. 1 and FIG. 2 represent the SEM photographs of the cross section of the warp.

Example 6

Figure 5:
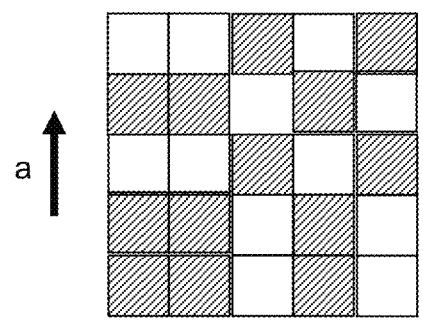
FIG. 5 is another example of a schematic view of a ripstop.

A woven fabric was made in the same manner as in Example 1 except using a polyethylene terephthalate fiber of 22 decitex and 12 filaments and having a double rip illustrated in FIG. 5 and a finished yarn density of 180 strands/2.54 cm in a longitudinal direction and 180 strands/2.54 cm in a lateral direction. In this case, CF is 1689. The obtained woven fabric was a woven fabric having all of thinness, flexibility, and high strength in the same way as the woven fabric of Example 1 and also had good molding workability when being made into a product for a stent graft of 14 Fr.

Example 7

A polyethylene terephthalate fiber of 22 decitex and 18 filaments as a fiber which did not constitute a ripstop portion and a polyethylene terephthalate fiber of 56 decitex and 18 filaments as a fiber constituting the ripstop portion were prepared and weaved into a plain woven fabric so that ripstop yarn was placed at intervals of three strands in both warp and weft. The woven fabric having a finished yarn density of 202 strands/2.54 cm in a longitudinal direction and 164 strands/2.54 cm in a lateral direction. In this case, CF is 2021. Then, only one roll was overheated to 160° C. to be subjected to calender treatment and was thermally set at 180° C. The obtained woven fabric was thin and had high strength and low permeability. Also, it had extremely good molding workability when being made into a product for a stent graft of 14 Fr because of being a soft and flexibly bending cloth.

Example 8

A woven fabric was made in the same manner as in Example 1 except that a fiber was a polyethylene terephthalate fiber of 33 decitex and 72 filaments and had a finished yarn density of 300 strands/2.54 cm in a longitudinal direction and 180 strands/2.54 cm in a lateral direction. The obtained woven fabric had an increased thickness but was excellent in permeability in comparison with the woven fabric of Example 1.

Example 9

A woven fabric was made in the same manner as in Example 1 except that a fiber was a polyethylene terephthalate fiber of 33 decitex and 72 filaments and had a finished yarn density of 153 strands/2.54 cm in a longitudinal direction and 153 strands/2.54 cm in a lateral direction. The obtained woven fabric had a decreased thickness and was excellent in flexibility in comparison with the woven fabric of Example 1.

Example 10

For the woven fabric obtained in Example 9, only one roll was further overheated to 160° C. to be subjected to calender treatment and was thermally set at 180° C. The obtained woven fabric had further suppressed permeability in comparison with the woven fabric of Example 1 and was also excellent in flexibility due to low fineness and low density. When the cross section of the obtained woven fabric was observed with an SEM, strands of yarn in a surface layer were transformed to be generally parallel to a surface (generally perpendicular to a thickness direction).

Comparative Example 1

A woven fabric was made in the same manner as in Example 1 except that a fiber was a polyethylene terephthalate fiber of 33 decitex and 72 filaments and had a finished yarn density of 330 strands/2.54 cm in a longitudinal direction and 130 strands/2.54 cm in a lateral direction. In comparison with Example 4 and Example 5, although it had high longitudinal density and a fine texture, it was poor in tensile strength in the lateral direction and also poor in permeability because of low lateral density.

Comparative Example 2

A woven fabric was made in the same manner as in Example 1 except that a fiber was a polyethylene terephthalate fiber of 44 decitex and 18 filaments and had a finished yarn density of 230 strands/2.54 cm in a longitudinal direction and 140 strands/2.54 cm in a lateral direction. The obtained woven fabric had an increased thickness and was excellent in permeability due to high yarn fineness but was poor in flexibility due to high single yarn fineness.

Comparative Example 3

Figure 6:
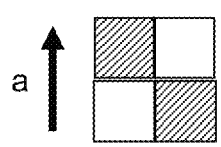
FIG. 6 is an example of a weave diagram of a plain woven fabric.

A woven fabric was made in the same manner as in Example 1 except that a fiber was a polyethylene terephthalate fiber of 44 decitex and 12 filaments and had a finished yarn density of 150 strands/2.54 cm in a longitudinal direction and 140 strands/2.54 cm in a lateral direction. Then, only one roll was overheated to 160° C. to be subjected to calender treatment and was thermally set at 180° C. FIG. 6 illustrates the weave diagram of the woven fabric. The obtained woven fabric had a large thickness and also had a tense texture although being subjected to calender working.

Comparative Example 4

A woven fabric was made in the same manner as in Example 1 except that a fiber was a polyethylene terephthalate fiber of 12 decitex and 1 filament and had a finished yarn density of 305 strands/2.54 cm in a longitudinal direction and 305 strands/2.54 cm in a lateral direction. In comparison with Example 1, a very thin base fabric was able to be obtained but had high permeability and was poor in flexibility although having high density.

Comparative Example 5

Figure 3:
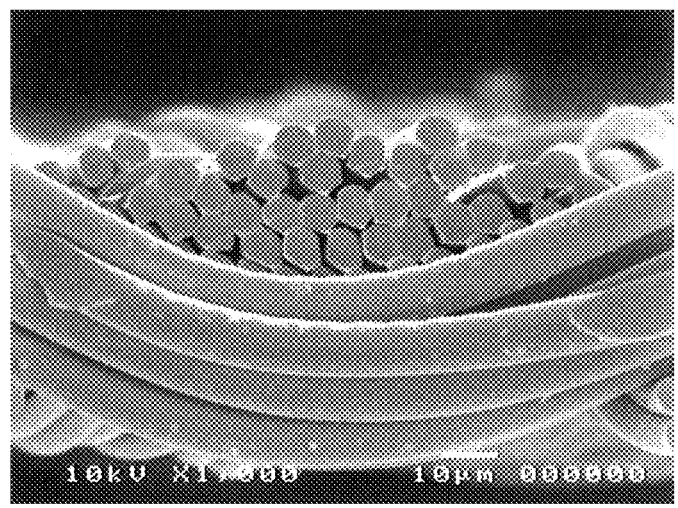
FIG. 3 is macrophotograph at 1000 times of an example of a cross-sectional view of a general woven fabric of which fibers on the outermost surface are not transformed.
Figure 4:
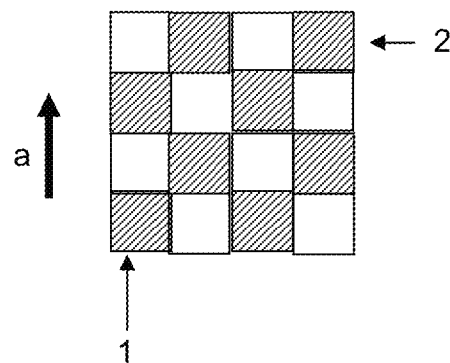
FIG. 4 is an example of a schematic view of a ripstop.

A woven fabric was made in the same manner as in Example 1 except that a fiber was a polyethylene terephthalate fiber of 22 decitex and 48 filaments and had a finished yarn density of 212 strands/2.54 cm in a longitudinal direction and 144 strands/2.54 cm in a lateral direction. It had high yarn density in comparison with Example 5 and Example 10, also had a higher cover factor than that of Example 5, and also had high strength, but had very high permeability. When the cross section of the obtained woven fabric was observed with an SEM, yarn in a surface layer had a round cross section similar to that of a center section. FIG. 3 represents an SEM photograph of the cross section of the warp.

Comparative Example 6

A woven fabric was made by the same treatment as in Example 1 except that a fiber was a polyethylene terephthalate fiber of 22 decitex and 630 filaments and had a finished yarn density of 160 strands/2.54 cm in a longitudinal direction and 174 strands/2.54 cm in a lateral direction. It had yarn density similar to those of Example 5 and Example 10 and moreover had further lower single yarn fineness than that of Example 10, but had a large thickness and also had flexibility similar to that of Example 10. When the cross section of the obtained cloth was observed with an SEM, yarn in a surface layer had a round cross section similar to that of a center section.

Comparative Example 7

A woven fabric was made in the same manner as in Example 1 except a finished yarn density of 120 strands/2.54 cm in a longitudinal direction and 100 strands/2.54 cm in a lateral direction. A base fabric which also had low yarn density and was thin and flexible was able to be obtained. However, it had low tensile strength and was also poor in permeability. When the cross section of the obtained cloth was observed with an SEM, yarn in a surface layer had a round cross section similar to that of a center section.

Comparative Example 8

A woven fabric was made in the same manner as in Example 1 except a finished yarn density of 300 strands/2.54 cm in a longitudinal direction and 200 strands/2.54 cm in a lateral direction. In the physical properties of the obtained woven fabric, a thickness was large, a texture was also tensed, and molding workability of a stent graft was poor.

Comparative Example 9

A woven fabric was made in the same manner as in Example 1 except a finished yarn density of 120 strands/2.54 cm in a longitudinal direction and 100 strands/2.54 cm in a lateral direction. The obtained woven fabric was quite poor in strength, also had high permeability, and did not satisfy an ability as a stent graft base fabric.

The physical properties of the obtained woven fabrics are listed in Tables 1 and 2.

TABLE 2

| | Permeability (mL/(min·cm$^2$)) | Bending resistance (mm) | Tensile strength (N/cm) Longitudinal | Tensile strength (N/cm) Lateral | Ripstop |
|---|---|---|---|---|---|
| Example 1 | 85 | 34 | 64.3 | 68.4 | Absence |
| Example 2 | 85 | 38 | 54.5 | 58.1 | Absence |
| Example 3 | 60 | 32 | 70.9 | 67.0 | Absence |
| Example 4 | 300 | 30 | 53.4 | 51.0 | Absence |
| Example 5 | 245 | 33 | 52.8 | 50.2 | Absence |
| Example 6 | 160 | 35 | 52.5 | 56.6 | Presence |
| Example 7 | 28 | 36 | 61.4 | 67.3 | Presence |
| Example 8 | 20 | 35 | 92.0 | 70.1 | Absence |
| Example 9 | 90 | 24 | 74.0 | 63.0 | Absence |
| Example 10 | 7 | 27 | 71.3 | 62.9 | Absence |
| Comparative Example 1 | 160 | 38 | 103 | 47.4 | Absence |
| Comparative Example 2 | 98 | 41 | 73.0 | 59.7 | Absence |
| Comparative Example 3 | 60 | 38 | 75.0 | 69.6 | Absence |
| Comparative Example 4 | 940 | 52 | 78.3 | 72.9 | Absence |
| Comparative Example 5 | 575 | 33 | 61.7 | 45.1 | Absence |
| Comparative Example 6 | 70 | 32 | 65.9 | 67.3 | Absence |
| Comparative Example 7 | ≥1000 | 25 | 39.1 | 41.1 | Absence |
| Comparative Example 8 | 26 | 38 | 76.2 | 64.7 | Absence |
| Comparative Example 9 | 884 | 30 | 39.1 | 41.1 | Absence |

REFERENCE SIGNS LIST a Longitudinal direction
1 Warp constituting ripstop
2 Weft constituting ripstop

The invention claimed is:

1. A base fabric for a stent graft which is a woven fabric comprising a fiber having a total fineness of 1 to 40 decitex and a single yarn fineness of 0.1 to 2.0 decitex, wherein the base fabric has a yarn density of 150 strands/2.54 cm or more in both longitudinal direction and lateral direction, a thick-

TABLE 1

| | Fiber | Single yarn fineness (decitex) | Texture | Finished yarn density (strands/2.54 cm) Warp | Finished yarn density (strands/2.54 cm) Weft | CF | Calender | Thickness (μm) |
|---|---|---|---|---|---|---|---|---|
| Example 1 | 22 decitex and 12 filaments | 1.83 | Plain weave | 250 | 200 | 2111 | No | 68 |
| Example 2 | 22 decitex and 12 filaments | 1.83 | Plain weave | 220 | 210 | 2017 | Yes | 55 |
| Example 3 | 22 decitex and 48 filaments | 0.46 | Plain weave | 300 | 200 | 2345 | No | 74 |
| Example 4 | 22 decitex and 12 filaments | 1.83 | Plain weave | 160 | 160 | 1501 | No | 40 |
| Example 5 | 22 decitex and 12 filaments | 1.83 | Plain weave | 160 | 160 | 1501 | Yes | 40 |
| Example 6 | 22 decitex and 12 filaments | 1.83 | Plain weave | 180 | 180 | 1689 | Yes | 49 |
| Example 7 | 22 decitex and 18 filaments | 1.22 | Plain weave | 202 | 164 | 2021 | Yes | 52 |
| Example 8 | 33 decitex and 72 filaments | 0.46 | Plain weave | 300 | 180 | 2757 | No | 85 |
| Example 9 | 33 decitex and 72 filaments | 0.46 | Plain weave | 153 | 153 | 1758 | No | 60 |
| Example 10 | 33 decitex and 72 filaments | 0.46 | Plain weave | 153 | 153 | 1758 | Yes | 50 |
| Comparative Example 1 | 33 decitex and 72 filaments | 0.46 | Plain weave | 330 | 130 | 2642 | No | 89 |
| Comparative Example 2 | 44 decitex and 18 filaments | 2.44 | Plain weave | 230 | 140 | 2454 | No | 114 |
| Comparative Example 3 | 44 decitex and 12 filaments | 3.70 | Plain weave | 150 | 140 | 1923 | Yes | 95 |
| Comparative Example 4 | 12 decitex and 1 filament | 12.00 | Plain weave | 305 | 305 | 2113 | No | 50 |
| Comparative Example 5 | 22 decitex and 48 filaments | 0.46 | Plain weave | 212 | 144 | 1670 | No | 65 |
| Comparative Example 6 | 22 decitex and 630 filaments | 0.04 | Plain weave | 160 | 174 | 1567 | No | 95 |
| Comparative Example 7 | 22 decitex and 12 filaments | 1.83 | Plain weave | 120 | 100 | 1032 | No | 40 |
| Comparative Example 8 | 22 decitex and 12 filaments | 1.83 | Plain weave | 300 | 200 | 2345 | No | 94 |
| Comparative Example 9 | 22 decitex and 12 filaments | 1.83 | Plain weave | 120 | 100 | 1032 | Yes | 44 | ness of 1 to 90 µm, and a tensile strength of 50.0 N/cm or more in both longitudinal direction and lateral direction;

wherein a surface of the woven fabric is subjected to calender working, the woven fabric is a plain woven fabric and further comprises a ripstop comprising a synthetic filament, and the woven fabric has a cover factor of 1500 to 4000.

2. The base fabric for a stent graft according to claim 1, comprising an outermost layer of at least one surface of the woven fabric, which outermost layer contains a fiber with a cross-sectional shape having a side which is generally parallel to a central line of a thickness of the woven fabric and/or a fiber with a cross-sectional shape having a major axis which is generally parallel to a central line of the thickness of the woven fabric.

3. The base fabric for a stent graft according to claim 1, wherein the woven fabric has a permeability of 250 mL/(cm$^2$·min) or less.

4. The base fabric for a stent graft according to claim 1, wherein a fiber constituting the ripstop is a fiber having a total fineness of 44 decitex or more.

5. The base fabric for a stent graft according to claim 1, wherein the fiber is multifilament.

6. A stent graft comprising the base fabric for a stent graft according to claim 1 and a stent.

* * * * *